(12) United States Patent
Daniel et al.

(10) Patent No.: US 11,723,723 B2
(45) Date of Patent: Aug. 15, 2023

(54) OUTCOME-BASED SPLINTING

(71) Applicant: DEPUY SYNTHES PRODUCTS, INC., Raynham, MA (US)

(72) Inventors: Steffan Daniel, Zuchwil (CH); Andre Furrer, Zuchwil (CH); Simon Bosshard, Bern (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 140 days.

(21) Appl. No.: 17/384,319

(22) Filed: Jul. 23, 2021

(65) Prior Publication Data

US 2021/0386457 A1     Dec. 16, 2021

Related U.S. Application Data

(62) Division of application No. 16/297,158, filed on Mar. 8, 2019, now Pat. No. 11,109,914.

(51) Int. Cl.
*A61B 17/64* (2006.01)
*A61B 34/10* (2016.01)
(Continued)

(52) U.S. Cl.
CPC .............. *A61B 34/10* (2016.02); *A61B 17/56* (2013.01); *A61B 17/64* (2013.01); *A61B 17/66* (2013.01); *A61B 17/72* (2013.01); *A61B 2017/0092* (2013.01); *A61B 2017/00862* (2013.01); *A61B 2017/00964* (2013.01); *A61B 2017/564* (2013.01); *A61B 2017/681* (2013.01); *A61B 2034/104* (2016.02); *A61B 2034/105* (2016.02)

(58) Field of Classification Search
CPC ... A61B 34/10–2034/108; A61B 17/60–17/66; A61B 2017/564
See application file for complete search history.

(56) References Cited

U.S. PATENT DOCUMENTS 5,546,942 A    8/1996  Zhang
8,860,753 B2  10/2014  Bhandarkar et al.
(Continued)

FOREIGN PATENT DOCUMENTS

WO    WO 2018/009736 A1    1/2018

*Primary Examiner* — Julianna N Harvey
(74) *Attorney, Agent, or Firm* — Kramer & Amado, P.C.

(57) ABSTRACT

A bone fracture fixation system including reference pins inserted into bone fragments of a patient in a first configuration and an image capture device configured to capture an image of the reference pins, and the bone fragments. The system includes a processor configured to receive and pre-process the captured image data. The processor pre-processes the image data by virtually re-positioning the reference pins in the first configuration into a second configuration, wherein the re-positioning virtually re-positions the bone fragments into normal alignment; and virtually generating a support device. The system includes a point-of-care production apparatus that produces a three-dimensional model of the virtually generated support device in a form that can be applied to the patient. The three-dimensional support device generated by the point-of-care production apparatus is configured to receive the reference pins in the first configuration; and simultaneously re-positions and fixes the bone fragments into normal alignment.

14 Claims, 6 Drawing Sheets

(51) Int. Cl.
  *A61B 17/56* (2006.01)
  *A61B 17/66* (2006.01)
  *A61B 17/72* (2006.01)
  *A61B 17/00* (2006.01)
  *A61B 17/68* (2006.01)

(56) References Cited

U.S. PATENT DOCUMENTS

| | | |
|---|---|---|
| 9,101,397 B2 | 8/2015 | Guthart et al. |
| 9,783,229 B2 | 10/2017 | Crawford et al. |
| 10,015,470 B2 | 7/2018 | Park |
| 2002/0194023 A1 | 12/2002 | Turley et al. |
| 2003/0004518 A1* | 1/2003 | Perren ............... A61B 17/6483 606/102 |
| 2008/0312702 A1* | 12/2008 | Schlienger ......... A61B 17/1735 606/329 |
| 2012/0136399 A1* | 5/2012 | Seifert .................. A61F 2/442 606/86 A |
| 2016/0235158 A1 | 8/2016 | Desjardins et al. |
| 2017/0249440 A1 | 8/2017 | Lang et al. |
| 2018/0280090 A1* | 10/2018 | Davies .................. A61B 34/10 |

* cited by examiner

OUTCOME-BASED SPLINTING

CROSS-REFERENCE TO RELATED APPLICATIONS

This application is a divisional application of application Ser. No. 16/297,158, filed Mar. 8, 2019, which is hereby incorporated herein by reference for all purposes.

BACKGROUND

1. Field

This disclosure relates generally to digitally-guided reduction and external fixation systems for fixing a bone fracture. More particularly, this disclosure relates generally to digitally guided reduction and external fixation systems that allow for reduction and fixation of a bone fracture in a single step.

2. Description of Related Art

External fixation traditionally entails the use of percutaneously placed pins and/or wires secured to an external scaffolding device to provide support for a fractured limb. Using this mechanism, a bone or joint can be stabilized during limb reconstruction. The technique presents many benefits compared to internal plates and intramedullary nails. External fixators cause less disruption of soft tissues, osseus blood supply and periosteum and are especially ideal for soft tissue management in cases of acute or chronic trauma wherein skin quality is compromised. Additionally, the temporary nature of the pins and wires make frames ideal for providing bone stability in cases of infection of the bone, where the presence of internal implants would make treatment of the infection more challenging. Furthermore, unlike internal plates, external fixators provide postoperative adjustability. External fixation may also be used in limb lengthening and deformity correction procedures.

Fracture management with external fixation involves placing longitudinal traction across a fractured limb to obtain a closed reduction and mounting a fixator while maintaining the reduction. External fixation devices are designed to assist in temporarily stabilizing the fracture and may be used for short periods of time until a more permanent solution is appropriate. Certain devices utilize a pin-to-bar frame construct. In utilization, the surgeon places half pins independently in safe corridors of the limb. Separate connecting bars are assembled to the pins and the bone segments are then manipulated to reduce the fracture. The connecting bars are then connected to one another until all points of fixation on the bone segment are incorporated.

Conventional external fixation devices require separate reduction and fixation components in the form of multiple connecting bars. Modified assemblies capable of reducing and fixating fractures would be beneficial to simplify the process of external fixation.

SUMMARY

The foregoing advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

In light of the present need for a simplified external fixation assembly, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments disclosed herein relate to a digitally-guided reduction and external fixation system for fixing a bone fracture including one or more reference pins configured to be inserted into one or more bone fragments of a patient in a first configuration and an image capture device configured to capture an image of the one or more reference pins in the first configuration, and the one or more bone fragments. The digitally-guided reduction and external fixation system additionally includes a virtual reduction and fixation device including a processor configured to execute instructions to receive the captured image data of the one or more reference pins in the first configuration, and the one or more bone fragments and pre-process the image data. The processor pre-processes the image data by virtually re-positioning the one or more reference pins in the first configuration into a second configuration, wherein the re-positioning of the one or more references pins into the second configuration virtually re-positions the one or more bone fragments into normal alignment; and virtually generating a support device, wherein the support device includes one or more apertures configured to receive the one or more reference pins in the second configuration. The processor then sends a description of the virtually generated support device to a point-of-care production apparatus. The point-of-care production apparatus is configured to produce a three-dimensional model of the virtually generated support device in a form that can be applied to the patient. The three-dimensional support device generated by the point-of-care production apparatus is configured to receive the one or more reference pins inserted into the one or more bone fragments of the patient in the first configuration; wherein the three-dimensional support device is configured to simultaneously re-position and fix the one or more bone fragments into normal alignment. In various embodiments, the system includes two or more reference pins, wherein the reference pins are threaded. The reference pins may be manufactured from a radiolucent material, such as a plastic-based material.

In various embodiments, the system further includes one or more scanning locators attached to the one or more reference pins at a proximal end. The scanning locators may be manufactured from a radiopaque material.

In various embodiments, the system further includes a locking device configured to fix the three-dimensional support device generated by the point-of-care production apparatus to the one or more reference pins inserted into the one or more bone fragments of the patient in the first configuration.

In various embodiments, the image capture device is an X-ray, MRI, CT, CBCT or ultrasound device. In various embodiments, the point-of-care production apparatus is a 3D printing device.

In various embodiments, the virtually generated support device further includes additional apertures that may be added at the discretion of the surgeon.

Various embodiments disclosed herein further relate to a method of reducing and fixating a bone fracture including inserting one or more reference pins into one or more bone fragments of a patient in a first configuration; capturing image data of the one or more reference pins in the first configuration, and the one or more bone fragments; and pre-processing the captured image data using a processor. The pre-processing step includes virtually re-positioning the one or more reference pins in the first configuration into a second configuration, wherein the re-positioning of the one or more references pins into the second configuration virtually re-positions the one or more bone fragments into normal alignment; and virtually generating a support device, wherein the support device includes one or more apertures configured to receive the one or more reference pins in the second configuration. The method additionally involves producing at the point-of-care a three-dimensional model of the virtually generated support device in a form that can be applied to the patient; applying the three-dimensional support device generated at the point-of-care to the one or more reference pins inserted into the one or more bone fragments of the patient in the first configuration; and simultaneously re-positioning and fixing the one or more bone fragments into normal alignment.

BRIEF DESCRIPTION OF THE DRAWINGS

In order to better understand various exemplary embodiments, reference is made to the accompanying drawings, wherein.

DETAILED DESCRIPTION

Embodiments described herein disclose a minimally-invasive treatment workflow with hardware and software elements for reducing and fixating bone fractures. Various embodiments combine principles of digital surgical planning and external fixation techniques to allow for bone fracture reduction and bone fracture fixation in a single step without the need for utilization of robotics. Various embodiments described herein further allow for point-of-care production of a patient-specific external fixation support device.

Figure 1:
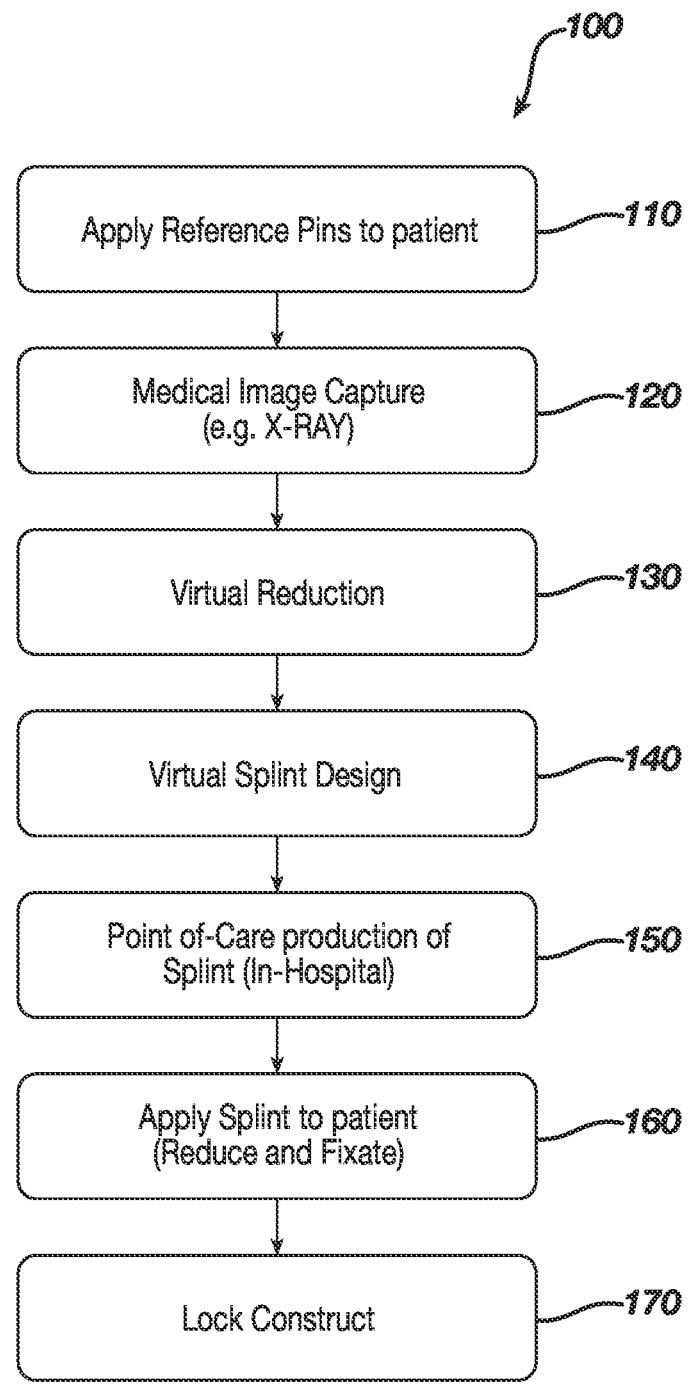
FIG. 1 is a flow diagram describing the steps of the digitally guided reduction and external fixation method.
Figure 2:
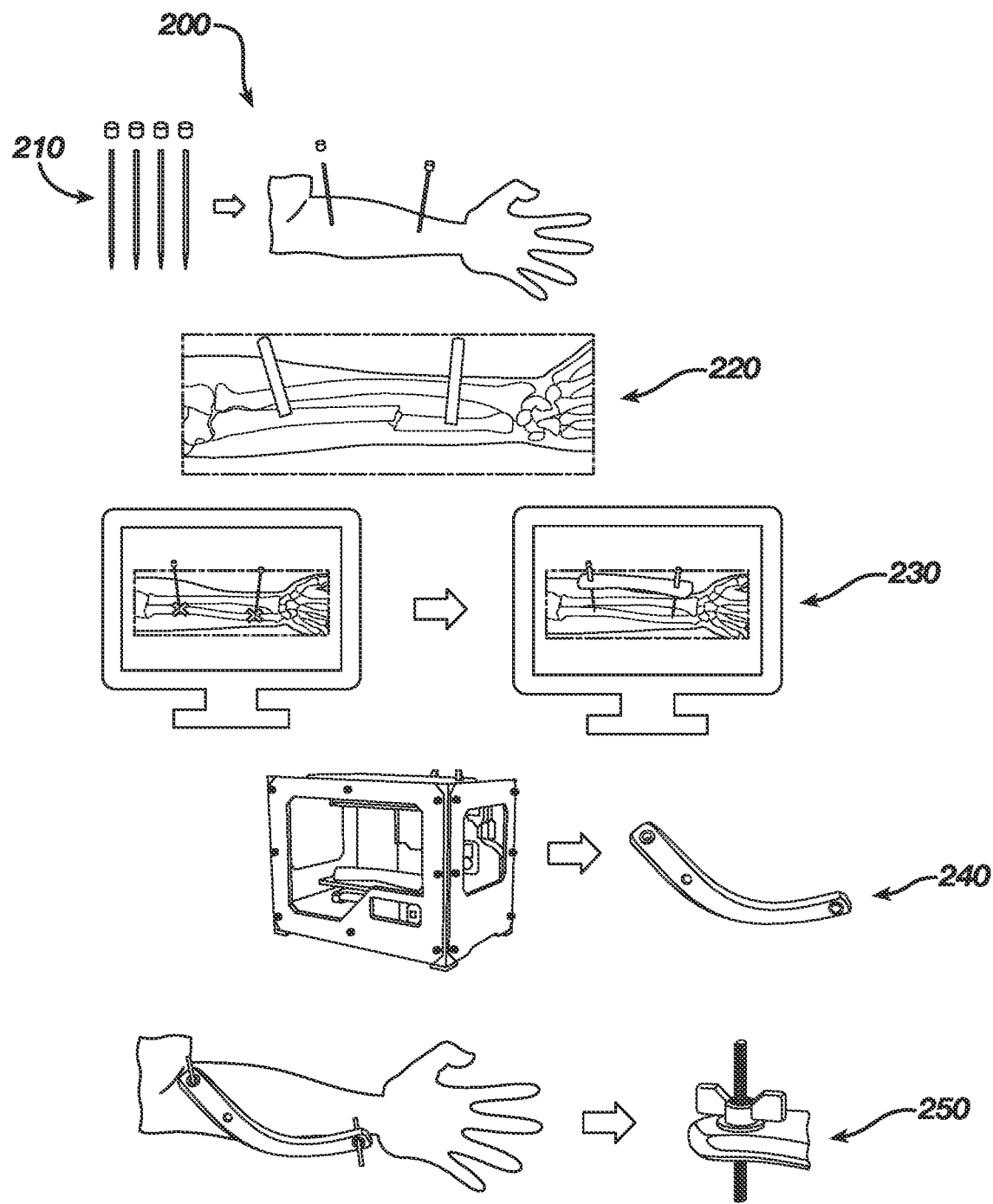
FIG. 2 is a flow diagram illustrating the digitally guided reduction and external fixation method.
Figure 5A:
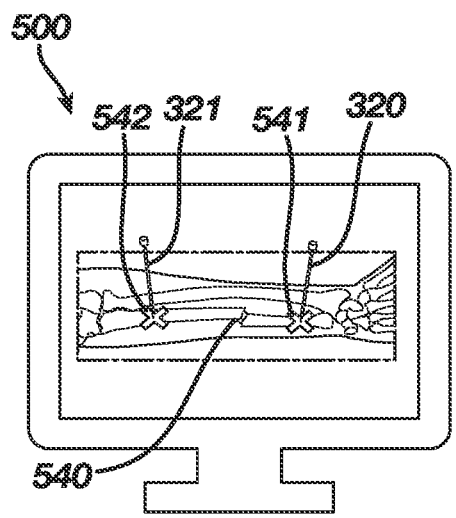
FIGS. 5A-5D illustrate the virtual reduction and virtual support device design steps of the digitally guided reduction and external fixation method.
Figure 5B:
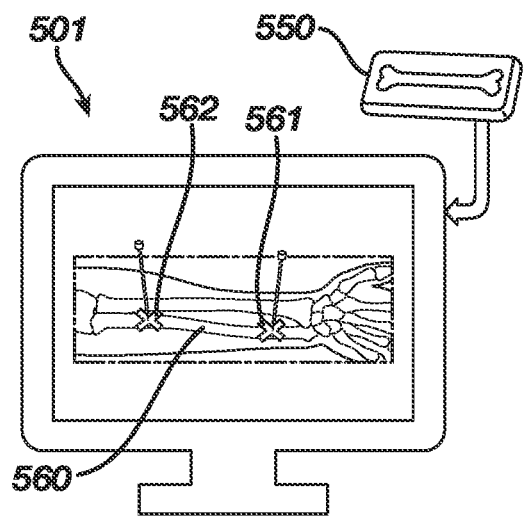

Referring now to the drawings, in which like numerals refer to like components or steps, there are disclosed broad aspects of various exemplary embodiments. FIGS. 1 and 2 diagram the steps of the digitally guided reduction and external fixation method 100, 200. In a first step 110, 210, reference pins 320 are applied to the fractured limb 330 of the patient (see also FIGS. 3A and 3B). In a second step 120, 220, the reference pins 320 are captured using a medical image capture device. In a third step 130, 230, a processor pre-processes the captured image data by virtually re-positioning the reference pins 320 in such a way as to reduce the bone fragments into normal alignment, as shown in FIGS. 5A and 5B. In a fourth step 140, 240, the processor generates a support device 530, wherein the support device 530 includes a first set of through-holes 531, 532 positioned to accommodate the reference pins 320, 321 after virtual fracture reduction. In some embodiments, the support device 530 may contain additional through-holes 533 to accommodate additional bone fixation pin 570. In a fifth step 150, 250, a support device 530 (see FIG. 6) is produced using a point-of-care production method. In a sixth step 160, 260, the support device 530 is applied to the patient (see FIG. 7). The support device 530 is configured to guide the reference pins 320, 321 to their final position, allowing fracture reduction in the operating room. Additional bone fixation pins 570 may be applied during the sixth step 160, 260. In a seventh step 170, 270 the reference pins 320, 321 and any additional bone fixation pins 570 are secured to the support device 530 using a locking device 930.

Figure 3A:
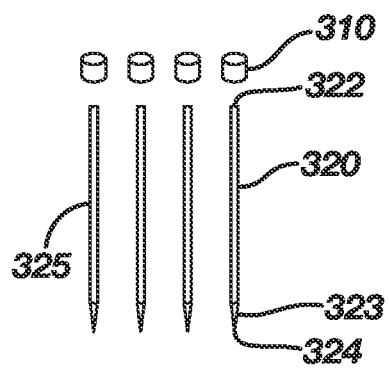
FIG. 3A illustrates a side view of the reference pins and scanning locators.

FIG. 3A provides a side view of the reference pins 320. The reference pins 320 include a proximal end 322 and a distal end 323. A scanning locator device 310 may be applied to the proximal end 322 of the reference pins 320 to provide an additional locator function for the reference pins 320. In various embodiments, the scanning locator device 310 may be applied by pushing or screwing the scanning locator device 310 onto the proximal end 322 of the reference pins 320.

In various embodiments, the scanning locator device 310 may be manufactured from any material that may be captured using an image capturing device, such as an X-ray, MRI, CT, CBCT or ultrasound device. In various embodiments, the scanning locator device 310 may be manufactured from a radiopaque material. Suitable radiopaque materials include stainless steel-, aluminum-, titanium-, silver-, bismuth-, and tantalum-based materials, radiopaque composite materials, such as radiopaque carbon fiber, or combinations thereof.

In various embodiments, the reference pins 320 may also be manufactured from any material that may be captured using an image capturing device. In various embodiments, the reference pins 320 may be manufactured from any materials capable of being viewed using a medical capture device. Suitable materials include radiopaque and radiolucent materials. Suitable radiolucent materials include plastic-based materials such as PEEK, polysulfone, polycarbonate, glass fiber, graphite fiber, polyetherimide, polyethersulfone, polyphenylsulfone, polyphenylsulfide and combinations thereof. The distal end 323 of the reference pins 320 may include a sharpened tip 324 to help facilitate penetration into a bone fragment. The shaft portion 325 of the reference pins may be threaded or unthreaded.

Figure 3B:
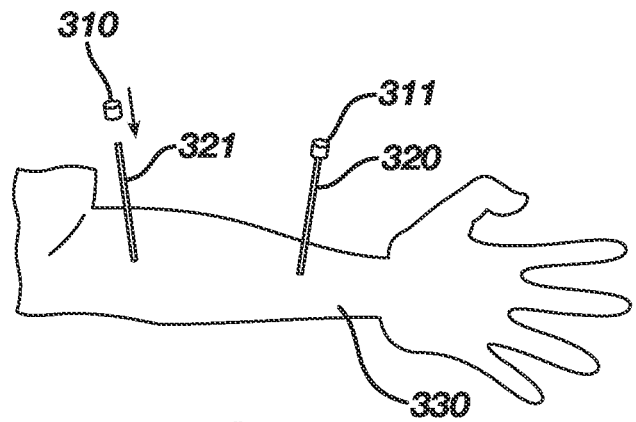
FIG. 3B illustrates the application step of the reference pins and scanning locators to a fractured limb.
Figure 4:
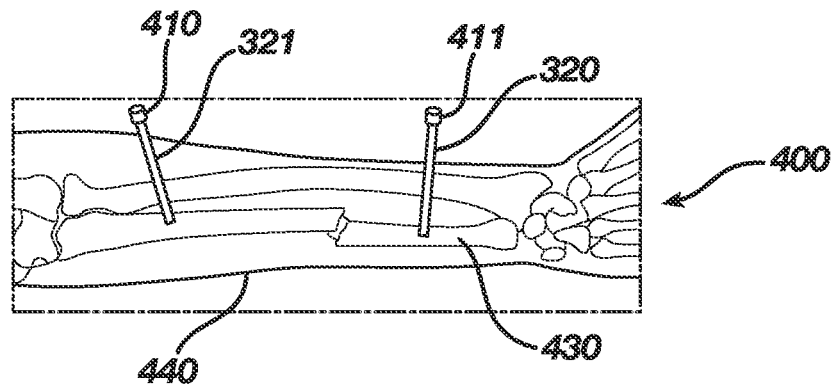
FIG. 4 illustrates the image captured during the image capture step of the digitally guided reduction and external fixation method.

FIG. 3B illustrates the application of the reference pins 320, 321 and scanning locator devices 310, 311 to a fractured forearm bone 330. As can be seen in FIG. 4, the reference pins 320, 321 and scanning locator devices 410, 411 may be inserted into the fractured bone 430 on either side of the fracture 440. FIG. 4 illustrates an image capture 400 generated during the medical image capture step 120. The image capture 400 may be generated using any suitable medical image capture technique, including X-ray, MRI, CT, CBCT or ultrasound.

Figure 5C:
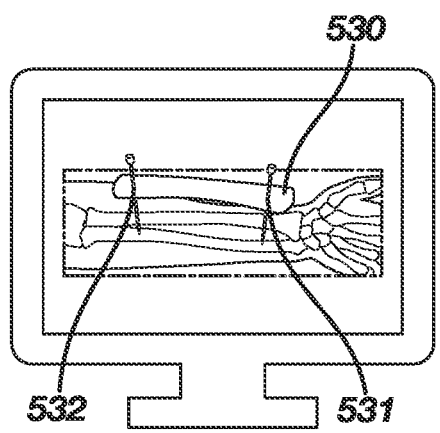
Figure 5D:
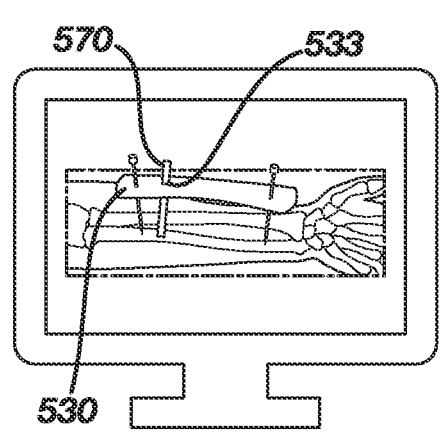

FIG. 5A illustrates an embodiment of the virtual reduction step 130 conducted using a first image capture 500 generated during the medical image capture step 120. In virtual reduction step 130, a processor is utilized to effect a virtual auto-reduction of a fracture 540 using the first image capture 500 and statistical bone data 550 to generate a second image capture 501, shown in FIG. 5B, showing the reduced bone 560 and final reference pin positions 561, 562. The processor is configured to collect data points characterizing the movement of the reference pins 320, 321 from first positions 541, 542 to the final reference positions 561, 562. The processor is then configured to generate a virtual support device 530 having a first set of through-holes 531,532 configured to accommodate the reference pins 320, 321 in final reference positions 561, 562 as shown in FIG. 5C. The processor is configured to generate a virtual support device 530 that is characterized by a design and contour that allows for reduction of the fracture 540. In some embodiments, the processor may be further configured to allow for the option of virtually generating an additional through-hole 533 to accommodate additional bone fixation pin 570 at the discretion of the user, as shown in FIG. 5D.

In various embodiments, the processor is a hardware device for executing software, particularly that which is stored in memory. The processor may be any custom made or commercially available processor, a central processing unit (CPU), an auxiliary processor among several processors associated with a computer, a semiconductor-based microprocessor (in the form of a microchip or chip set), a macroprocessor, or generally any device for executing software instructions.

Figure 6:
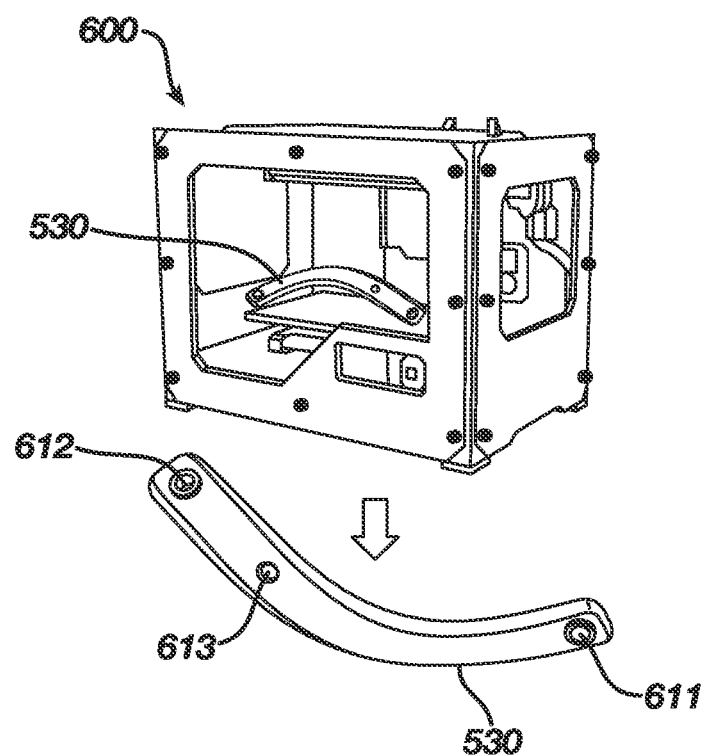
FIG. 6 illustrates the point-of-care support device production step of the digitally guided reduction and external fixation method.

FIG. 6 illustrates the point-of-care production step 150 wherein the virtual support device 530 is translated, using a processor and a point-of-care production device 600, into a three-dimensional support device 530. As can be seen in FIG. 6, the three-dimensional support device 530 contains a first set of through-holes 611, 612 configured to accommodate the reference pins 320, 321 and an additional through-hole 613 to accommodate additional bone fixation pin 570. The point-of-care production device 600 may be a 3-D printer or any other device that allows for immediate translation of a two-dimensional image to a three-dimensional model. The three-dimensional support device 530, may be manufactured from any suitable materials of sufficient rigidity to support reduction and external fixation of a bone fracture. Such materials include standard plate fixation plate materials, such as plastic materials, metallic materials, and composites. Suitable plastic materials include thermoplastic materials including acrylic, ABS, Nylon, PLA, polycarbonate (PC), polyethylene materials and combinations thereof. Suitable metallic materials include titanium, stainless steel and the like; and suitable composite materials include carbon fiber and the like.

Figure 7:
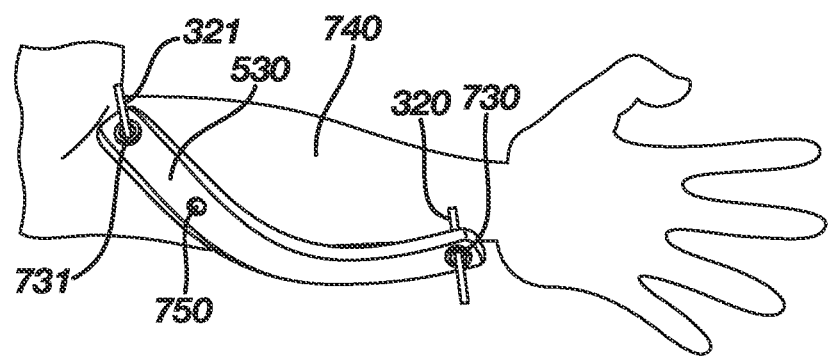
FIG. 7 illustrates the support device application step of the digitally guided reduction and external fixation method.

FIG. 7 shows the application of the three-dimensional support device 530 over reference pins 320, 321. The reference pins 320, 321 are inserted into through holes 730, 731, respectively. In this embodiment, application of the three-dimensional support device 530 reduces and fixates a fracture of the forearm 740. In other embodiments, the three-dimensional support device 530 may be configured to be applied to reduce and fixate a fracture of any bone of the patient. The three-dimensional support device 530 shown in FIG. 7 includes the additional through-hole 750 configured to accommodate additional bone fixation pin 570.

Figure 8A:
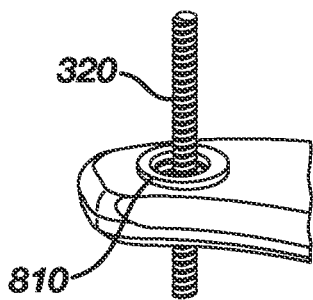
FIGS. 8A-8B illustrate different configurations of reference pin insertion into the through holes of the support device.
Figure 8B:
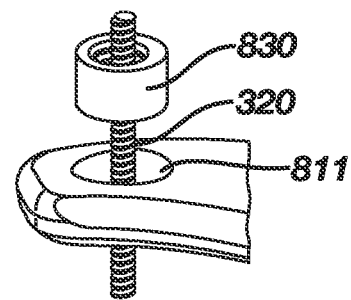

FIGS. 8A and 8B show embodiments of different insertion configurations for the reference pin 320 through through-holes 810, 811. In FIG. 8A, the through-hole 810 is sized to threadably engage the threaded reference pin 320. In FIG. 8B, the reference pin 320 first threadably engages an insert 830. The reference pin 320 and insert 830 construct is then inserted into a through-hole 811 sized to accommodate the insert 730.

Figure 9A:
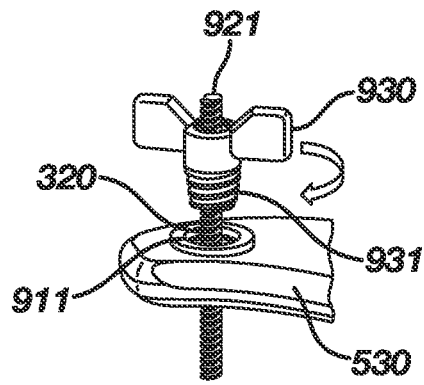
FIGS. 9A-9D illustrate different embodiments of locking devices used to secure the support device to the reference pins.
Figure 9B:
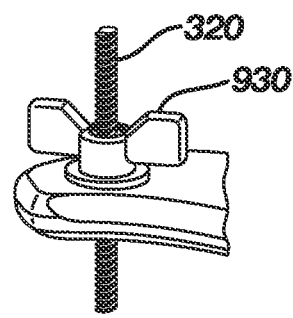

FIGS. 9A and 9B illustrate a first embodiment of a locking device 930 configured to secure the reference pin 320 into through-hole 911 of three-dimensional support device 910. The locking device 930 is threadably secured to threaded reference pin 320 at a proximal end 921 and rotated in a clockwise direction until a distal end 931 of the locking device 930 is secured in the through-hole 911, as shown in FIG. 9B. More specifically, the locking device 930 contains a threaded portion 931 at a distal end configured to threadably engage complementary threads contained on the inner surface of through-hole 911.

Figure 9C:
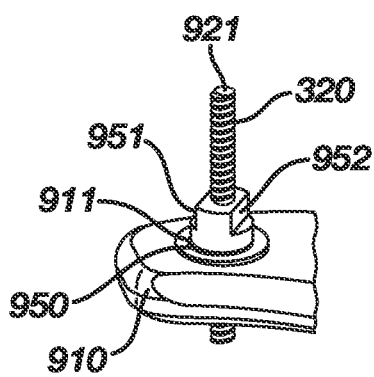
Figure 9D:
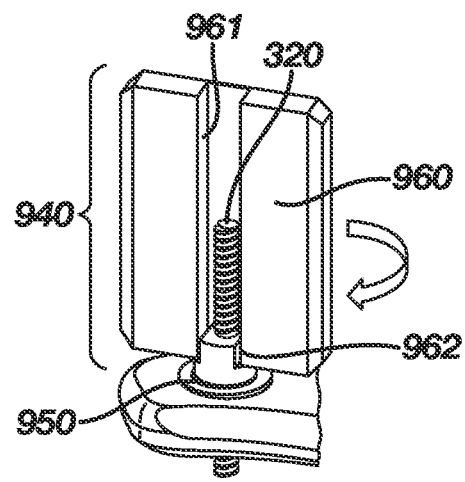

FIGS. 9C and 9D illustrate an alternative embodiment of a locking device 940 configured to secure the reference pin 320 to the through hole 911 of the three-dimensional support device 530. The locking device 940 includes a locking nut 950 configured to threadably engage the reference pin 320 at a proximal end 921. The locking nut 950 contains a first groove 951 and a second groove 952. The locking device 940 additionally includes a locking key 960 having a channel 961 configured to slidably receive the reference pin 320 and further configured to engage the grooves 951, 952 of the locking nut 950 at a distal end 962. The locking key 960, when turned in a clockwise direction, secures the locking nut 950 into the through-hole 911.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of reducing and fixating a bone fracture comprising
   inserting one or more reference pins into one or more bone fragments of a patient in a first configuration;
   capturing image data of the one or more reference pins in the first configuration, and the one or more bone fragments,
   pre-processing the captured image data using a processor by
      virtually re-positioning the one or more reference pins in the first configuration into a second configuration, wherein a re-positioning of the one or more reference pins into a second configuration virtually re-positions the one or more bone fragments into normal alignment;
      virtually generating a support device, wherein the support device comprises one or more apertures configured to receive the one or more reference pins in the second configuration and the support device is configured to simultaneously achieve reduction and long-term fixation by repositioning and fixing the one or more bone fragments into normal alignment;

producing, at a point-of-care, a three-dimensional model of the virtually generated support device in a form that can be applied to the patient;

applying the three-dimensional model generated at the point-of-care to the one or more reference pins inserted into the one or more bone fragments of the patient in the first configuration; and simultaneously re-positioning and fixing the one or more bone fragments into normal alignment.

2. The method of claim 1, wherein the method comprises inserting two or more reference pins.

3. The method of claim 2, wherein the two or more reference pins are threaded.

4. The method of claim 1, wherein the reference pins are manufactured from a radiolucent material.

5. The method of claim 4, wherein the one or more reference pins are manufactured from a plastic-based material.

6. The method of claim 5, wherein the plastic-based material is selected from a group consisting of PEEK, polysulfone, polycarbonate, glass fiber, graphite fiber, polyetherimide, polyethersulfone, polyphenylsulfone, polyphenylsulfide and combinations thereof.

7. The method of claim 1, wherein the method further comprises:

attaching one or more scanning locators to the one or more reference pins positioned in the first configuration at a proximal end.

8. The method of claim 7, wherein the one or more scanning locators are manufactured from a radiopaque material.

9. The method of claim 8, wherein the radiopaque material is selected from a group consisting of stainless steel, aluminum, titanium, silver, bismuth, and tantalum materials, radiopaque composite materials or combinations thereof.

10. The method of claim 1, wherein the method further comprises:

locking the three-dimensional model to the one or more reference pins inserted into the one or more bone fragments of the patient in the first configuration.

11. The method of claim 1, wherein the image data is captured using an image capture device.

12. The method of claim 11, wherein the image capture device is an X-ray, MRI, CT, CBCT, or ultrasound device.

13. The method of claim 1, wherein the three-dimensional model produced at the point-of-care is produced using a 3D printing device or a desktop CNC mill.

14. The method of claim 1, wherein the method further comprises:

adding additional apertures during virtual generation of the support device at the discretion of a surgeon.

\* \* \* \* \*